United States Patent [19]
Kondou

[11] Patent Number: 5,667,573
[45] Date of Patent: Sep. 16, 1997

[54] COATING COMPOSITION FOR PREPARING SOLID PREPARATIONS AND SOLID PREPARATIONS

[75] Inventor: Tsutomu Kondou, Kanagawa, Japan

[73] Assignee: Mitsubishi Chemical Corporation, Tokyo, Japan

[21] Appl. No.: 679,264

[22] Filed: Jul. 12, 1996

[30] Foreign Application Priority Data

Jul. 13, 1995 [JP] Japan .................................. 7-199294

[51] Int. Cl.$^6$ .................... C09D 101/00; C09D 101/28
[52] U.S. Cl. .................... 106/194.2; 106/203.2; 424/480
[58] Field of Search .............. 106/194.2, 203.2; 424/480

[56] References Cited

U.S. PATENT DOCUMENTS

| | | | |
|---|---|---|---|
| 2,226,823 | 12/1940 | Kropscott | 106/194.2 |
| 3,539,380 | 11/1970 | Johnson | 106/194.2 |
| 4,579,259 | 4/1986 | Hirao et al. | 106/194.2 |
| 4,678,516 | 7/1987 | Alderman et al. | 106/194.2 |
| 4,816,298 | 3/1989 | Alderman et al. | 106/194.2 |
| 5,393,333 | 2/1995 | Trouve | 106/194.2 |

FOREIGN PATENT DOCUMENTS

| | | |
|---|---|---|
| 62-5910 | 1/1987 | Japan . |
| 21138117 | 5/1990 | Japan . |

*Primary Examiner*—David Brunsman
*Attorney, Agent, or Firm*—Sughrue, Mion, Zinn, Macpeak & Seas

[57] ABSTRACT

The present invention provides a sugar coating composition comprising erythritol, a water-soluble cellulose, and an aqueous medium; and a solid preparation comprising a center core of a medicine or a food, etc. coated with the sugar coating composition. The sugar coating composition provides solid preparations with a smooth texture and satisfactory taste and which has a low viscosity even at room temperature and is therefore easy to handle.

12 Claims, No Drawings

COATING COMPOSITION FOR PREPARING SOLID PREPARATIONS AND SOLID PREPARATIONS

FIELD OF THE INVENTION

This invention relates to a sugar coating composition for preparing solid preparations such as powders, granules, tablets, etc. in the field of foodstuffs and pharmaceuticals; and solid preparations coated with the sugar coating composition. More particularly, it relates to non-hygroscopic solid preparations having a satisfactory texture and a sugar coating composition which is low in calories, does not cause dental caries, and has excellent handling properties in the coating operation.

BACKGROUND OF THE INVENTION

Bitter medicines, foods which are apt to change their shape with temperature rise, etc. have been supplied after forming a coating layer with a sugar coating composition so as to be taken or eaten with ease.

Most of the conventional sugar coating compositions consist mainly of sugar, a binder, and water. Improvements have been added to these compositions in taste and adhesion to the center core to be coated which contains a medicine or a food material (hereinafter inclusively referred to as a "center").

As the binder used in the conventional sugar coating compositions to enhance adhesion of the coating layer to the center, gelatinizers such as gelatin and agar and gums such as gum arabic, xanthane gum, and guar gum have been widely used. For example, JP-A-62-5910 (the term "JP-A" as used herein means an "unexamined published Japanese patent application") discloses a sugar coating composition containing hydroxypropylmethylcellulose and a water-soluble cellulose derivative as binders and sucrose, and JP-A-2-138117 discloses a sugar intermediate coating layer comprising hydroxypropylmethylcellulose and mannitol.

Although gelatin has satisfactory binding properties, sugar-coated tablets prepared by using gelatin undergo reduction in disintegrability and also browning of color with the passage of time.

While excellent in extending properties, gum arabic has insufficient binding properties. If used in an increased amount, the texture becomes rough when dried.

Water-soluble cellulose as a binder, when coated on a center to form sugar-coated tablets, provides a smooth texture. However, water-soluble cellulose itself is unpleasant to the taste and has been limited in use.

Further, there is a problem that the viscosity of the sugar coating composition prepared by using these conventional binders increases when it is applied to a center, making the coating operation difficult. In addition, the multi-layered structure in order to achieve good adhesiveness of the sugar coating layer and good texture results in too large sugar-coated preparations.

SUMMARY OF THE INVENTION

The inventors have conducted extensive study on the preparation of a sugar coating composition which is free from these disadvantages. As a result, they have found that a sugar coating composition using erythritol and water-soluble cellulose shows advantageous for handling in coating operation due to its low viscosity and provides coated solid preparations having a smooth texture and satisfactory adhesion between the sugar coat and the center, which can make the sugar coating layer thin. The present invention was accomplished based on these findings.

That is, the gist of the present invention resides in a sugar coating composition comprising an aqueous medium, erythritol and a water-soluble cellulose, and in a coated solid preparation comprising a center core of a medicine or a food material coated with the sugar coating composition.

DETAILED DESCRIPTION OF THE INVENTION

The invention is described below in detail.

The term "coated solid preparation" as used herein is intended to inclusively mean centers having a sweet taste surface layer. The coated solid preparations include pharmaceutical coated solid preparations, coated confectioneries or foods.

Erythritol is a kind of tetrose alcohols, which is easily soluble in water and ready to crystallize to provide beautiful white crystals. It has 75 to 85% of the sweetness of sucrose and feels fresh and cool in the mouth. Erythritol rarely undergoes browning with time or increase in temperature, and it is low in calories and non-hygroscopic.

The erythritol content in the sugar coating composition is subject to variation depending on the kind or quality of the center to be coated and is decided accordingly. For assuring satisfactory adhesion to the center and a good texture, it is preferably 10 to 50% by weight, still preferably 20 to 30% by weight, based on the total weight of the sugar coating composition.

The water-soluble cellulose used in the present invention is obtained by partially or wholly etherifying the hydroxyl group of natural cellulose with organic chloride (e.g., alkali chloride, hydroxyalkyl chloride, aminoalkyl chloride) to form ether structures, and its appearance is white or yellowish white powder. Examples of the etherified substituents include alkyl groups (e.g., methyl and ethyl), hydroxyalkyl groups (e.g., hydroxymethyl and hydroxyethyl), aminoalkyl groups, and hydroxyaminoalkyl groups. The water-soluble cellulose may have one or more types of the above-described substituents. As the water-soluble cellulose, partially etherified ones are preferred. The degree of substitution is appropriately decided depending on the type of the substituents. As the water-soluble cellulose, hydroxyalkyl group containing water-soluble cellulose is preferable, and hydroxyalkylalkylcellulose (i.e., cellulose derivatives having hydroxyalkyl side groups and alkyl side groups) is particularly preferable. As the hydroxyalkylalkylcellulose, those having the hydroxyalkyl group having 1 to 4 carbon atoms in the alkyl moiety thereof with the alkyl group being methyl are preferable, and hydroxypropylmethylcellulose (referred to as "HPMC" hereinafter) is particularly preferable. The most preferred HPMC is 2-hydroxypropylmethylcellulose. HPMC is derived from cellulose by etherifying the hydroxyl group thereof with hydroxypropyl chloride and methyl chloride. The preferred hydroxypropyl group content of HPMC is in the range of from 4 to 12, more preferably from 7 to 12% by weight, and the preferred methyl group content of HPMC is in the range of from 20 to 30, more preferably from 28 to 30% by weight based on the natural cellulose used for the etherification.

The water-soluble cellulose content in the sugar coating composition is arbitrarily selected according to the kind of the center to be coated. In order to assure satisfactory adhesion to the center, it is preferably 1 to 10% by weight, still preferably 5 to 10% by weight, based on the total weight of the sugar coating composition. If the water-soluble cellulose content is less than 1%, the composition tends to have insufficient adhesion. The too high water-soluble cellulose content is not preferable, since the water-soluble cellulose has a tendency to swell and gel on water absorption, which causes increase in the viscosity of the sugar coating composition, requires an extended period of time of the coating operation and, in some cases, causes water-soluble cellulose precipitates which provide coated solid preparations having a rough texture.

It is particularly desirable for the sugar coating composition to have an erythritol content of 20 to 30% by weight and a water-soluble cellulose content of 5 to 10% by weight, based on the total weight of the sugar coating composition, with the weight ratio of water-soluble cellulose to erythritol being 1:2 to 1:7. In this embodiment, coated solid preparations extremely excellent in both adhesion and texture can be obtained.

Crystal growth of erythritol in the coating operation may be controlled by using another sugar alcohol in combination with erythritol in such an amount that does not impair the non-hygroscopicity of erythritol. Usable sugar alcohols include maltitol, sorbitol, xylitol, and reducing saccharified starch. The amount of another sugar alcohol is preferably 1 to 100 parts by weight based on 100 parts by weight of erythritol.

If desired, the sugar coating composition may further contain other sugars, such as sucrose, lactose, maltose, xylose, coupling sugar, and palatinose, as far as the characteristics of the composition, such as non-hygroscopicity, are not impaired.

The medium of the sugar coating composition is an aqueous medium, usually water.

If desired, the sugar coating composition may contain other binders, such as dextrin, starch, gelatin, other cellulose derivatives, polyvinyl alcohol, etc. in addition to water-soluble cellulose. Where a white coated solid preparation is desired, starch (e.g., potato starch, corn starch, wheat starch, and rice starch), calcium carbonate, talc, or titanium oxide may be dispersed in the sugar coating composition.

The material and weight of the center can be arbitrarily chosen according to the object. For example, in the preparation of medicines in the form of granules, powders, pills or tablets or coated confectioneries, such as sugar-coated chewing gum, sugar-coated chocolate, spherical or disk-shaped centers each weighing about 0.1 to 3 g and measuring about 1 to 10 mm in diameter are generally used.

The solid preparation according to the present invention includes the resulting sugar-coated tablets, film-coated tablets, coated confectioneries, as well as all the other coated materials having surface layer tasting sweetness.

The step of coating centers with the sugar coating composition of the present invention can be carried out in a conventional manner. For improved workability, the sugar coating composition is preferably maintained at a temperature of from 10° to 40° C. during the coating operation. If the temperature exceeds 40° C., water-soluble cellulose tends to precipitate and would make the texture of the resulting coated solid preparations rough. Therefore, the coating is preferably conducted at a temperature of not higher than 40° C.

The coating step is carried out by, for example, putting centers in a rotating container, and adding the sugar coating composition either intermittently or continuously in small portions while rotating the container. The amount of the sugar coating composition to be added is adjusted appropriately according to the surface area of the centers and the object of the coated solid preparations. The sugar coating composition of the present invention may also be sprayed to the center.

After uniform application of the sugar coating composition to the surface of the centers, drying is carried out usually in the rotating container. Drying is carried out by blowing air at a temperature of 20° to 80° C., a relative humidity of 35 to 65%, and a rate of 2 to 8 m/sec. Once the sugar coated layer is dried, the sugar coating composition is again scattered thereon, followed by drying. The application of the composition and the drying are repeated several times to obtain resulting coated solid preparations. If desired, the resulting coated solid preparations may be given a gloss finish by addition of wax, shellac, etc.

The amount of the dry coated layer may appropriately be decided depending on the density of the center and coated layer, and is generally from 0.1 to 500 parts by weight, preferably from 1 to 300 parts by weight, and more preferable from 5 to 100 parts by weight, based on 100 parts by weight of the center. The coated layer in an amount less than 0.1 part by weight is not preferable, since sufficient coating of the center would not be achieved or, when the center has undesirable taste (e.g., bitter), the sufficient improvement of the taste of the center by coated layer would not be achieved. The coated layer exceeding 500 parts by weight is not preferable, since the resulting sugar-coated preparation becomes too large. The sugar-coated preparations thus obtained have a weight of from about 0.1 g to about 10 g and a diameter of from about 1 mm to about 50 mm.

The present invention will now be illustrated in greater detail with reference to Examples, but it should be understood that the present invention is not construed as being limited thereto as long as it does not depart from the gist of the present invention.

The centers used in the following Examples were prepared by mixing 30 parts by weight of erythritol (hereinafter abbreviated as ET) and 70 parts by weight of lactose and molding the mixture by a tabletting machine. The viscosity (unit: cP) of the sugar coating compositions prepared was measured with an E type viscometer manufactured by Tokyo Keiki K. K. at 25° C.

All the numbers used for the constituents mean percents by weight based on the total sugar coating composition. The compositions having a zero content of water-soluble cellulose or ET are for comparison.

Unless otherwise indicated, all parts, ratios, percents, and the like are by weight.

EXAMPLE 1

A sugar coating composition (250 g) having an ET concentration of 30% and a varied HPMC content as shown in Table 1 below was prepared. In a 10 l-volume rotating drum having a radius of 15 cm, 500 g of centers each weighing 2 g (an average diameter: 5 mm) was put in the drum, and a 20 g portion of the sugar coating composition was applied onto the centers while rotating the drum at 26 rpm and spreading was repeated so that the composition might be spread all over the surface of the centers. The centers were then dried by blowing air having a temperature of 40° C. and a relative humidity of 45% at a rate of 4 m/sec for 10 minutes. Application of the sugar coating composition and the following drying were repeated 5 times to prepare sugar-coated tablets.

TABLE 1

| HPMC      | 0   | 1  | 2  | 4  | 6   | 7   | 12  |
|-----------|-----|----|----|----|-----|-----|-----|
| ET        | 30  | 30 | 30 | 30 | 30  | 30  | 30  |
| Water     | 70  | 69 | 68 | 66 | 64  | 62  | 58  |
| Viscosity | 2.5 | 5  | 9  | 28 | 50  | 114 | 259 |
| Texture   | x   | o  | o  | o  | ⊚   | ⊚   | Δ   |
| Adhesion  | x   | o  | o  | o  | ⊚   | ⊚   | o   |

Standards for Evaluation:
1) Texture:
⊚ Glossy and smooth
o Smooth
Δ Partly rough
x Rough
2) Adhesion:
A glass tube having a diameter of 1 cm and a height of 100 cm was placed upright, and a coated solid preparation was dropped from the open top of the tube. The condition of the sugar coated layer of the fallen tablet was observed with the naked eye and graded as follows.
⊚ The coated layer did not come off even after falling twice.
o The coated layer developed cracks but did not come off even after falling twice.
Δ Part of the coated layer came off after falling twice.
x The coated layer came off on falling once.

The tablets coated by the sugar coating composition having an ET concentration of 30% and containing no HPMC had a rough texture, and the coated layer came off the center on falling once. The coated layer of the same sugar coating composition having added thereto 1 to 10% of HPMC exhibited satisfactory texture and adhesion to the center. The coated layer of the sugar coating composition having an HPMC concentration of 12% had a rough texture due to precipitated HPMC.

The sugar coating compositions according to the invention were easy to handle because they had sufficiently low viscosity at room temperature and required no heating to about 40° C.

EXAMPLE 2

Coated solid preparations were prepared in the same manner as in Example 1, except for fixing the HPMC concentration at 6% and varying the ET content as shown in Table 2 below.

TABLE 2

| HPMC      | 6  | 6  | 6  | 6  | 6  | 6  | 6  |
|-----------|----|----|----|----|----|----|----|
| ET        | 8  | 16 | 20 | 24 | 32 | 40 | 50 |
| Water     | 86 | 78 | 74 | 70 | 62 | 52 | 44 |
| Viscosity | 16 | 20 | 23 | 28 | 36 | *  | *  |
| Texture   | ⊚  | ⊚  | ⊚  | ⊚  | o  | o  | Δ  |
| Adhesion  | Δ  | o  | ⊚  | ⊚  | ⊚  | o  | o  |

Note: * The viscosity was not measurable because ET in the sugar coating composition slightly precipitated.

Coated solid preparations having excellent texture and adhesion to the center were obtained by using a sugar coating composition containing HPMC and ET. In particular, the coated layer formed by using a sugar coating composition having an HPMC content of 6% by weight, an ET content of 20 to 30% by weight, and an HPMC to ET weight ratio of 1:2 to 1:7 was extremely excellent in both texture and adhesion as well as handling properties.

EXAMPLE 3

Coated solid preparations were prepared in the same manner as in Example 1, except for fixing the HPMC concentration at 8% and varying the ET content as shown in Table 3 below.

TABLE 3

| HPMC      | 8  | 8  | 8  | 8  | 8  | 8  | 8  |
|-----------|----|----|----|----|----|----|----|
| ET        | 8  | 16 | 20 | 24 | 32 | 36 | 40 |
| Water     | 84 | 76 | 72 | 68 | 60 | 56 | 50 |
| Viscosity | 31 | 44 | 61 | 73 | 86 | *  | *  |
| Texture   | ⊚  | ⊚  | ⊚  | ⊚  | o  | Δ  | Δ  |
| Adhesion  | Δ  | o  | ⊚  | ⊚  | ⊚  | ⊚  | o  |

Note: * The viscosity was not measurable because ET in the sugar coating composition slightly precipitated.

Coated solid preparations having excellent texture and adhesion to the center were obtained by using a sugar coating composition containing HPMC and ET. In particular, the coated layer formed by using a sugar coating composition having an HPMC content of 8% by weight, an ET content of 20 to 30% by weight, and an HPMC to ET weight ratio of 1:2 to 1:7 is extremely excellent in both texture and adhesion as well as handling properties.

EXAMPLE 4

Coated solid preparations were prepared in the same manner as in Example 1, except for using a sugar coating composition having the composition shown in Table 4 below.

TABLE 4

| HPMC           | 0    | 10   | 20   | 30   | 40   |
|----------------|------|------|------|------|------|
| ET             | 6    | 6    | 6    | 6    | 6    |
| PEG-600        | 1.2  | 1.2  | 1.2  | 1.2  | 1.2  |
| Titanium oxide | 1.2  | 1.2  | 1.2  | 1.2  | 1.2  |
| Talc           | 0.9  | 0.9  | 0.9  | 0.9  | 0.9  |
| Water          | 90.7 | 80.7 | 70.7 | 60.7 | 50.7 |
| Texture        | ⊚    | ⊚    | ⊚    | ⊚    | Δ    |
| Adhesion       | ⊚    | o    | ⊚    | ⊚    | o    |
| Taste*         | x    | ⊚    | ⊚    | ⊚    | ⊚    |

Note:
*⊚ Satisfactory with fresh sweetness
x Odor of medicine

Coated solid preparations according to the present invention had satisfactory taste free from odor of medicine. The coated layer was satisfactory in texture and adhesion to the center.

EXAMPLE 5

Coated solid preparations were prepared in the same manner as in Example 1, except for using ET, sucrose, or mannitol as sugar components according to Table 5 below. The viscosity of the sugar coating compositions was measured at 40° C.

TABLE 5

| Composition: | | | | | | | | | | | | | |
|---|---|---|---|---|---|---|---|---|---|---|---|---|---|
| Et | 15 | 23 | 30 | — | — | — | — | — | — | 15 | 15 | 15 | 15 |
| Mannitol | — | — | — | 15 | 23 | 30 | — | — | — | 15 | 0 | 15 | 0 |
| Sucrose | — | — | — | — | — | — | 15 | 23 | 30 | 0 | 15 | 0 | 15 |
| HPMC | 7 | 7 | 7 | 7 | 7 | 7 | 7 | 7 | 7 | 7 | 7 | 0 | 0 |
| Water | 78 | 70 | 63 | 78 | 70 | 63 | 78 | 70 | 63 | 63 | 63 | 70 | 70 |
| Viscosity | 32 | 43 | 53 | 39 | * | * | 39 | 44 | 180 | 18 | 66 | 2.6 | 2.0 |
| Texture | ◎ | ◎ | ◎ | Δ | x | x | ○ | ○ | ○ | ○ | ○ | Δ | Δ |
| Adhesion | ◎ | ◎ | ◎ | Δ | Δ | Δ | ◎ | ◎ | ◎ | ○ | ◎ | x | ○ |
| Taste | ○ | ○ | ○ | Δ | Δ | Δ | ◎ | ◎ | ◎ | ○ | ◎ | ○ | ○ |
| Color Change** | ◎ | ◎ | ◎ | ○ | ○ | ○ | x | x | x | ○ | x | ○ | x |
| Others | | | | | | | | | | | | | ** |

Note:
*The viscosity was not measurable due to precipitation of mannitol.
**Did not apt to dry Color change was evaluated as follows.

Two grams of each sugar was weighed out, put in a test tube, and kept in a drier at 150° C. for 1.5 hours. After cooling, 8 ml of water was added to dissolve the sugar, and the absorbance at 420 nm and 720 nm was measured with a spectrophotometer. The degree of coloration was calculated by the following equation.

$$\text{Coloration} = \text{absorbance after heating} (420\,\text{nm} - 720\,\text{nm}) - \text{absorbance before heating} (420\,\text{nm} - 720\,\text{nm})$$

Evaluation:

◎ . . . Degree of coloration=0

○ . . . 0<Degree of coloration<1 x . . . Degree of coloration ≧ 1

The coated solid preparations of the present invention exhibited a smooth texture and satisfactory adhesion between the sugar coated layer and the center. Since the sugar coating composition of the invention has excellent color change resistance, it is possible to raise the temperature of the sugar coating composition to reduce its viscosity (as is apparent by comparison with Example 1), to thereby improve handling properties, which is of great advantage for the preparation of coated solid preparations.

EXAMPLE 6

In a 1 l-volume rotating drum having a radius of 5 cm and a number of rotation of 26 rpm, 50 g of calcium tablets (centers) consisting of 90% of calcium hydrogenphosphate, 5% of calcium lactate, and 5% of calcium citrate, each weighing 0.3 g and having an average diameter of 7 mm was put in the drum, and coated with the following sugar coating composition in the same manner as in Example 1. The amount of the sugar coating composition used and the total weight of the resulting coated solid preparations, measured after drying in vacuo at 75° C. for 4 hours, are shown in the table.

| Sugar-Sugar coating composition (wt %): | |
|---|---|
| Erythritol | 10 |
| Sucrose | 10 |
| HPMC | 7 |
| Water | 63 |

TABLE 6

| Sugar coating composition (g) | Coated Tablets (g) | Coating Weight (mg/tablet) | Sensory Test |
|---|---|---|---|
| 0 | 50 | 0 | bitter |
| 3 | 50.7 | 4.2 | slightly sweet |
| 5 | 51.5 | 6.6 | slightly sweet |
| 8 | 51.7 | 10.2 | slightly sweet |
| 10 | 52.0 | 12.0 | sweet |
| 15 | 52.8 | 16.8 | sweet |
| 20 | 53.2 | 19.2 | sweet |

Materials used in Examples are shown below.

ET: A product of Nikken Chemicals Co., Ltd.

Sucrose: Granular sugar produced by Mitsui Sugar Co., Ltd.

Mannitol: A product of Kishida Kagaku K. K.

HPMC: TC-5, a product of Shin-Etsu Chemical Co., Ltd.

PEG-600: Polyethylene glycol produced by Nippon Oil and Fats Co., Ltd.

The sugar coating composition containing erythritol and HPMC according to the present invention exhibits satisfactory adhesion to the center to provide coated solid preparations with a smooth texture and satisfactory taste. The sugar coating composition of the present invention has a lower viscosity even at room temperature in comparison with conventional sugar coating compositions containing other saccharides, so that it is easy to handle without requiring heating, which is greatly beneficial for the preparation of coated solid preparations. In addition, the sugar coated layer can be made thin and the resulting solid preparation has improved taste.

While the invention has been described in detail and with reference to specific embodiments thereof, it will be apparent to one skilled in the art that various changes and modifications can be made therein without departing from the spirit and scope thereof.

What is claimed is:

1. A coating composition, which comprises erythritol, a water-soluble cellulose, and an aqueous medium.

2. A coating composition according to claim 1, wherein said water-soluble cellulose is a hydroxylalkyl group-containing water-soluble cellulose.

3. A coating composition according to claim 2, wherein said hydroxylalkyl group-containing water-soluble cellulose is a hydroxyalkylalkylcellulose.

4. A coating composition according to claim 3, wherein said hydroxyalkylalkylcellulose has a hydroxyalkyl group having 1 to 4 carbon atoms in the alkyl moiety thereof.

5. A coating composition according to claim 4, wherein the hydroxyalkyl moiety of said hydroxyalkylalkylcellulose is a 2-hydroxyalkyl group having 2 to 4 carbon atoms.

6. A coating composition according to claim 3, wherein the alkyl moiety other than the alkyl moiety of the hydroxyalkyl group is a methyl group.

7. A coating composition according to claim 3, wherein the hydroxyalkylalkylcellulose is hydroxypropylmethylcellulose.

8. A coating composition according to claim 1, wherein said composition has a water-soluble cellulose content of 1 to 10% by weight and an erythritol content of 10 to 50% by weight based on the total weight of the coating composition.

9. A coating composition according to claim 8, wherein said composition has a water-soluble cellulose content of 5 to 10% by weight, an erythritol content of 20 to 30% by weight based on the total weight of the coating composition, and a water-soluble cellulose to erythritol weight ratio of 1:2 to 1:7.

10. A solid preparation which comprises a center core of a medicine or a food and a surface coated layer comprising erythritol and a water-soluble cellulose.

11. A solid preparation according to claim 10, wherein the weight ratio of the surface coated layer to the center core is from 1:100 to 300:100.

12. A solid preparation according to claim 10, wherein the weight ratio of the surface coated layer to the center core is from 5:100 to 100:100.

* * * * *